United States Patent
Fox et al.

(10) Patent No.: US 7,089,747 B2
(45) Date of Patent: Aug. 15, 2006

(54) PRESSURE REDUCTION APPARATUS AND METHOD

(75) Inventors: Richard B. Fox, Mesa, AZ (US); Richard B. Gadberry, Phoenix, AZ (US)

(73) Assignee: Honeywell International, Inc., Morristown, NJ (US)

( * ) Notice: Subject to any disclaimer, the term of this patent is extended or adjusted under 35 U.S.C. 154(b) by 160 days.

(21) Appl. No.: 10/788,763

(22) Filed: Feb. 27, 2004

(65) Prior Publication Data

US 2005/0188700 A1   Sep. 1, 2005

(51) Int. Cl.
*F02C 6/08* (2006.01)
*G01N 30/00* (2006.01)

(52) U.S. Cl. .................. 60/782; 60/785; 73/23.41; 73/23.42

(58) Field of Classification Search ............... 60/736, 60/727, 782, 785; 73/763.86, 23.41, 23.42, 73/763

See application file for complete search history.

(56) References Cited

U.S. PATENT DOCUMENTS

| | | | |
|---|---|---|---|
| 868,931 A | 10/1907 | Kuazmaut, Jr. | |
| 2,083,036 A | 8/1937 | Rogers | |
| 2,103,838 A | 12/1937 | Bach | |
| 2,230,098 A | 1/1941 | Wurzburgar | |
| 3,446,425 A * | 5/1969 | Cleeves | 415/1 |
| 3,593,023 A | 7/1971 | Fullerton et al. | |
| 3,866,850 A | 2/1975 | Skoch et al. | |
| 3,868,474 A | 2/1975 | Hasselmann | |
| 4,109,509 A | 8/1978 | Cramer et al. | |
| 4,135,399 A | 1/1979 | Kaczmarek et al. | |
| 4,137,647 A | 2/1979 | Clark, Jr. | |
| 4,285,245 A * | 8/1981 | Kennedy | 73/861 |
| 4,632,019 A | 12/1986 | Whiteman | |
| 4,756,200 A | 7/1988 | Ramsner et al. | |
| 4,863,202 A | 11/1989 | Wahl | |
| 4,893,848 A | 1/1990 | Melcher | |
| 5,437,199 A | 8/1995 | Kaplan | |
| 5,553,895 A | 9/1996 | Karl et al. | |
| 5,621,180 A | 4/1997 | Simon et al. | |
| 5,637,792 A | 6/1997 | Kimura et al. | |
| RE35,639 E * | 10/1997 | Vander Heyden et al. | 374/36 |
| 5,750,999 A | 5/1998 | Fox | |
| 5,765,612 A | 6/1998 | Morin | |
| 5,794,986 A | 8/1998 | Gansel et al. | |
| 5,907,109 A | 5/1999 | Tedeschi | |
| 5,921,592 A | 7/1999 | Donnelly | |
| 8,138,521 | 10/2000 | Besch et al. | |

(Continued)

FOREIGN PATENT DOCUMENTS

DE    101 62 278 A1    7/2003

(Continued)

*Primary Examiner*—Ted Kim
(74) *Attorney, Agent, or Firm*—Ingrassia Fisher & Lorenz

(57) ABSTRACT

A pressure reduction apparatus is disclosed. Air at high pressure and temperature may be drawn from a source such as a bleed valve of a gas turbine engine that supplies the air to an airplane interior. The air is passed to a pressure reduction vessel. The vessel has sufficient volume such that the high pressure air, upon entering the vessel, will reduce in temperature and pressure. The pressure reduction apparatus allows the air to depressurize and drop in temperature to near ambient conditions. Upon exiting the pressure reduction apparatus, the air is at a temperature and pressure sufficient to allow the air to be sampled and analyzed by conventional equipment used for testing for airborne impurities such as semivolatile compounds ad particulates.

26 Claims, 5 Drawing Sheets

U.S. PATENT DOCUMENTS

| | | |
|---|---|---|
| 6,217,441 B1 | 4/2001 | Pearman et al. |
| 6,226,852 B1 | 5/2001 | Gundel et al. |
| 6,230,573 B1 * | 5/2001 | Schulten et al. ......... 73/863.86 |
| 6,418,801 B1 | 7/2002 | Lewis |
| 6,471,682 B1 | 10/2002 | Tucker |
| 2001/0045000 A1 | 11/2001 | Gundel et al. |
| 2002/0071786 A1 | 6/2002 | Schreiber, Jr. et al. |
| 2002/0153725 A1 | 10/2002 | Myers |
| 2002/0189332 A1 | 12/2002 | Schell |
| 2003/0008341 A1 | 1/2003 | Spurrell |
| 2003/0012696 A1 | 1/2003 | Millancourt |

FOREIGN PATENT DOCUMENTS

| | | |
|---|---|---|
| WO | WO 97/36176 | 10/1997 |
| WO | PCT/US2005/005973 | 8/2005 |

* cited by examiner

PRESSURE REDUCTION APPARATUS AND METHOD

FIELD OF THE INVENTION

The present invention relates to high volume air sampling. More particularly the invention relates to methods and equipment used for taking high volume air samples from an enclosed volume such as that encountered in an aircraft cabin. In particular the present invention also relates to a high volume air sampling train, adapters, and associated ductwork. Still more particularly the invention relates to an apparatus and method for first reducing the pressure and temperature in an air sample drawn from a gas turbine engine.

BACKGROUND OF THE INVENTION

Air samplers are finding increased application in a variety of uses. One such application deals with the transportation industry. For example, passengers may be subject to noxious smells or gases or other airborne impurities when traveling in enclosed vehicles such as trains, motor coaches, or airplanes.

When an event occurs during which passengers are subject to odors, smoke, gases, or other undesirable airborne impurities, it is desirable to perform some kind of test or sampling. The testing or sampling of the air supply may be done for several reasons. It may be desired to repeat the incident of impure air flow in order to sample the air and thus trace the source of impurity. Additionally, the testing or sampling may be performed in part to certify that, once corrected, the vehicle in question is again supplying clean air to passengers.

In the example of a modern passenger jetliner, air supply to the interior cabin often begins with the gas turbine engines. In the typical structure of a gas turbine engine, including those used in industrial, marine, vehicle, as well as aerojet applications, air enters the engine inlet and first passes through a series of compressor stages such as a low pressure stage and a high pressure stage. The air then passes through a combustion chamber and, in exiting the engine, crosses turbines such as high pressure and low pressure turbines. However, a significant portion of air that enters the engine inlet passes around the compressors, combustion chamber and turbines, this is called fan air. Additionally air in the compressors may be bled off for deicing and other pneumatic applications through bleed valves. Bleed valves are typically used to select air at a desired pressure within the gas turbine engine during varying power conditions. Alternatively air may be supplied to the air craft cabin through a separate compressor not directly associated with the engine. Environmental control systems used in commercial airliners often draw air from either the bleed valves or ram air. This air may then pass through ductwork, pumps, temperature controls, and other air handling equipment before being vented into the passenger cabin.

Present in these turbine propulsion engines as well as the APU's (auxiliary power units) are fluid sealing systems. Sealing systems typically work to contain materials such as lubricants and hydrocarbons within the engine body. For example sealing systems are employed within a gas turbine engine to prevent trace elements of materials such as fuel or lubricant from leaking from the engine and into the bleed air. However, such sealing systems are not always totally effective, and as a result there may be leakage of fuel or lubricant into the bleed air. Hence hydrocarbons and lubricants within the engine may be the source of semivolatile compounds that result in odors and noxious impurities that may be harmful or unpleasant to the passengers. Hydrocarbons for example can oxidize and produce smoke and particulates in the air flowing into the cabin.

Previous methods used to measure contaminants in engine bleed air have either been inconclusive or have given false readings. One such method incorporates a polyvinylchloride filter to collect a sample of the bleed air followed by looking for the presence of oil by using a black light to make the oil droplets fluoresce. Another method includes the use of a large, stainless steel coil chilled to about −100 degrees F. to condense matter in the bleed air. The condensed matter is then flushed from the coil, evaporated with a solvent (freon) and weighed. In a third method, the bleed air is flowed through absorption tubes in which residue is collected on silica gel, charcoal, or molecular sieves and then evaluated by gas chromatography/mass spectroscopy. The residue can also be analyzed by combusting its organic matter, and measuring the carbon dioxide formed with a flame ionization detector or nitrogen phosphorous detector.

Presently, there is no known equipment available that is designed to sample high volumes of air from a closed system. In particular there is no known equipment designed to take high volume air samples from the interior chamber of a closed aircraft fuselage. Accordingly there is a need for a high volume air sampler that can screen for particulate, volatile, and semivolatile materials present in the air sample.

In a closed environment, such as the fuselage interior of a commercial jet airplane, traditional methods of taking air samples face difficulties. In the typical known method for taking air samples a collector is exposed to the environment where it is desired to take an air sample. One end of the collector is open to the atmosphere and an opposite end of the collector is attached to a pump (typically with an intervening hose). Running the pump pulls a vacuum which serves to pull air through the collector.

The difficulty of such an arrangement in a closed environment is that pulling a vacuum to take the air sample is resisted by the closed nature of where the air sample is in the plane interior. Thus it is difficult to take large volume air samples with this arrangement. However, large volume air samples are sometimes preferred where for example the concentration of the suspected contaminant is relatively low. In such a case it is often necessary to sample a large volume of air in order to capture a sufficient quantity of the contaminant in order to subject the impurity to analysis.

Hence there is a need for a high volume air sampler that addresses one or more of the above-noted objectives. That is there is a need for a high volume air sampler capable of drawing a sufficiently large air sample to detect the presence of certain airborne impurities; and/or that is capable of drawing an air sample in a closed environment of minimal weight and/or that is capable of drawing air samples that pass through the enclosed interior of an airplane fuselage and/or that is compact and portable so as to be used in different airplane shapes and sizes. The high volume air sampler disclosed herein addresses one or more of these needs.

SUMMARY OF THE INVENTION

The present invention provides a pressure reduction apparatus that is light in weight, and effects a reduction in temperature and pressure in air. The pressure reduction apparatus receives air at a relatively high starting temperature and pressure, as for example, from a gas turbine engine, or more particularly from a bleed valve of a gas turbine engine, and by expanding the volume of this air, allows the air to reduce in temperature and pressure relative to the starting temperature and pressure. The size of the pressure reduction apparatus is selected to allow the degree of pressure reduction and temperature cooling desired, for example to approximately ambient or atmospheric temperatures and pressures.

In one embodiment, and by way of example only, there is provided a pressure reduction apparatus comprising: a hollow vessel defining an interior and an exterior; a valve affixed to the vessel to allow air to enter the vessel; and a port on the vessel to allow air to exit the vessel. The valve on the vessel prevents air from exiting the vessel through the valve and may be a ball valve. The apparatus may further include a pressure gauge for measuring air pressure in the interior of the vessel and a temperature gauge for measuring air temperature in the interior of the vessel.

In a further embodiment, and by way of example only, there is provided a vessel for reducing the temperature and pressure in air drawn from a gas turbine engine comprising: a vessel body having an exterior and a substantially hollow interior; a valve affixed to the vessel body providing fluid communication between the exterior and the interior of said vessel body wherein the valve permits air to enter the vessel body and prevents air from exiting the vessel body; and the vessel body further defines an exit port providing fluid communication between the interior and the exterior of said vessel body. The vessel body is of sufficient dimension such that air entering the vessel body is reduced in pressure and temperature in the interior of the vessel body. Moreover the interior of the vessel body defines a sufficient volume such that air admitted to the vessel body from a gas turbine engine is sufficiently reduced in temperature and pressure at the interior of said vessel body for testing for the presence of inorganic compounds. Alternatively the interior of the vessel body defines a sufficient volume such that air admitted to the vessel body from a gas turbine engine bleed valve is reduced in temperature and pressure at the interior of said vessel body to approximately ambient conditions.

In preferred embodiments the vessel body is composed in whole or part of aluminum or aluminum alloy.

In a further embodiment and by way of example only there is provided an apparatus for reducing the temperature and pressure in air drawn from a bleed valve of a gas turbine engine comprising: a vessel having an exterior and a substantially hollow interior; a valve affixed to the vessel allowing air to enter the vessel and preventing air from exiting said vessel through said valve which may be a ball valve; the vessel further defines a port to allow air to exit the vessel; a hollow duct with two ends, a first end of the duct drawing air from a bleed valve of a gas turbine engine and a second end of the duct attached to the valve; a hollow tubing with two ends, a first end of the tubing affixed to the port of the vessel, and a second end leading air to the exterior of vessel, for example to further sampling or testing equipment located downstream from the vessel.

In preferred embodiments the hollow duct comprises a carbon impregnated Teflon or carbon impregnated silicone.

The apparatus may have a vessel that further defines an aperture providing fluid communication between the exterior and the interior of the vessel, which, for example may be used to draw air samples from the interior of the vessel.

Other independent features and advantages of the pressure reduction apparatus will become apparent from the following detailed description, taken in conjunction with the accompanying drawings which illustrate, by way of example, the principles of the invention.

DETAILED DESCRIPTION OF A PREFERRED EMBODIMENT

Reference will now be made in detail to exemplary embodiments of the invention, examples of which are illustrated in the accompanying drawings. Wherever possible, the same reference numbers will be used throughout the drawings to refer to the same or like parts.

High Volume Air Sampler

Figure 1:
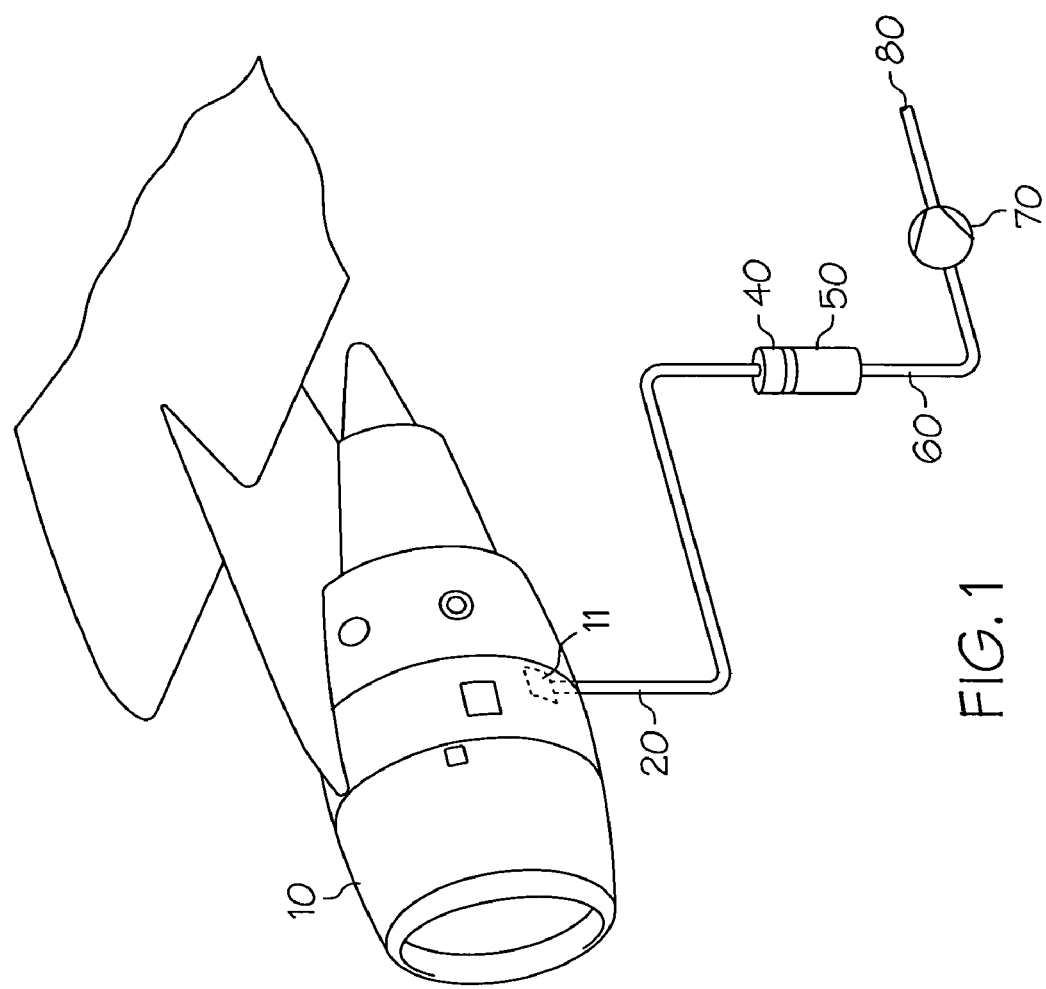
FIG. 1 is a schematic view of a high volume air sampler in accordance with an embodiment of the invention.

Referring now to FIG. 1 there is shown a schematic view of an embodiment of the high volume air sampler system. A preferred embodiment of the high volume air sampler system comprises multiple components. The high volume air sampler begins with an air source. In one application of the system, the air supply source is a gas turbine engine 10 such as found on a commercial airliner. The air supply may be taken, for example, from fan air in the engine compartment. Alternatively and preferably, the air is taken from a bleed valve 11 located on the engine 10, or from a location within the aircraft environmental control system. Thirdly, air can be ducted from a confined location such as a cockpit air where there is insufficient room to locate a high volume collection system.

Still referring to FIG. 1 source hose 20 draws air from bleed valve 11. Source hose 20 is preferably an electrically conductive flexible tubing such as for example flexible stainless steel or carbon loaded teflon tubing. Flexible conduit may be adapted and bent such that the tubing may transport the air from the engine compartment, through configurations in the aircraft body if necessary, to a desired location.

In one preferred embodiment, source hose 20 transfers air from bleed valve 11 to a receptor. The receptor comprises collar 40 and a sample canister 50.

Preferably the high volume air sampler is adapted to accept standard sized industry fittings for air sampling equipment. A three inch diameter sampling system is one such preferred size. Thus source hose 20 and collar 40 are preferably sized to accept such sized fittings although other sizes are possible.

Figure 2:
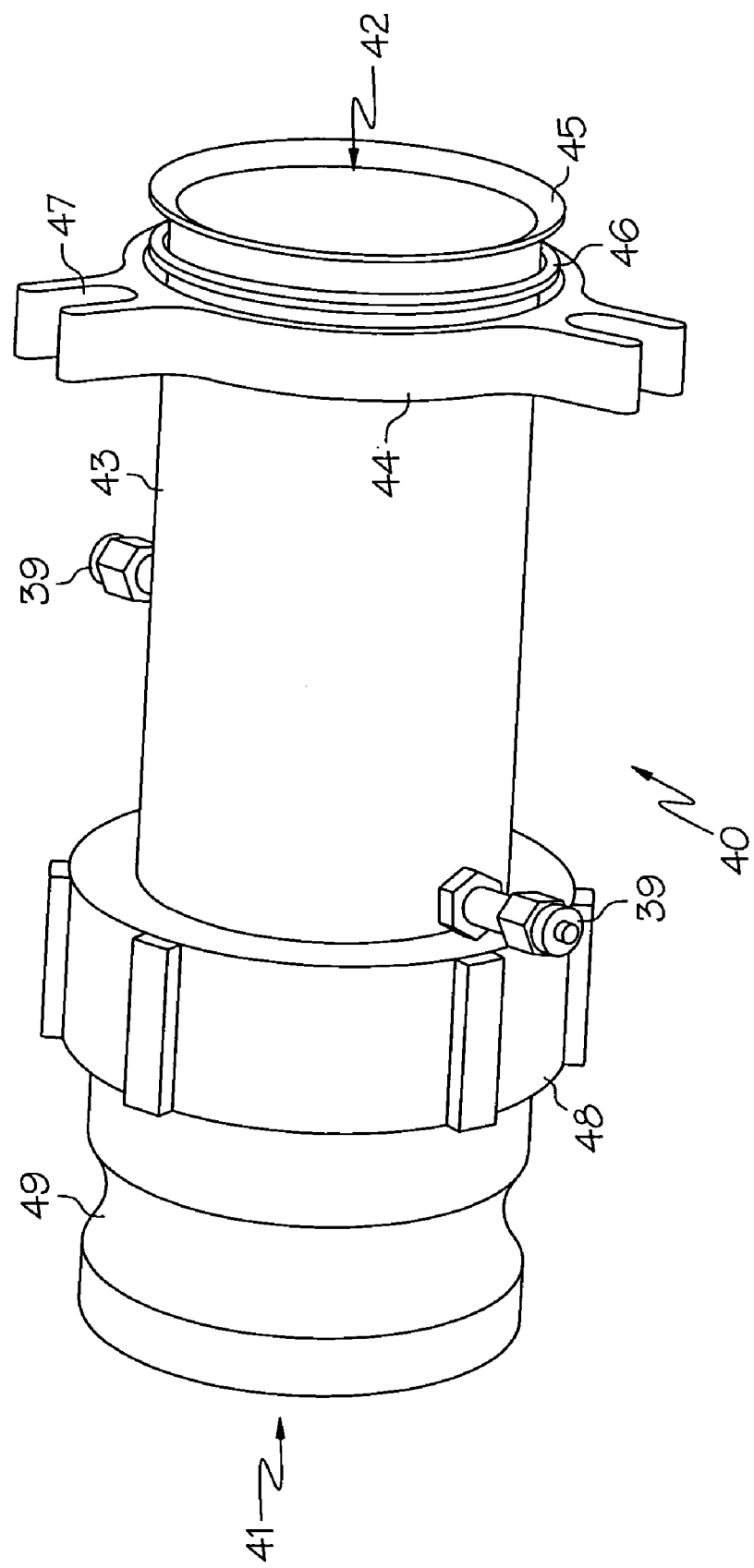
FIG. 2 is a detailed view of a collar in accordance with an embodiment of the invention.

Referring now to FIG. 2 collar 40 comprises a structure whereby source hose 20 may be adapted to supply air to canister 50 through collar 40. In a preferred embodiment collar 40 is a hollow structure having an interior and an exterior that allows fluid communication therethrough. Collar 40 includes body 43 clamp 44 and seal 46. Preferably collar 40 is constructed in whole or part of a light, durable material such as aluminum or aluminum alloy. While collar 40 can be constructed in various configurations, it is preferred to manufacture collar 40 from aluminum tubing. When so manufactured, collar 40 is generally cylindrical in shape and circular in cross section.

Still referring to FIG. 2 collar 40 has an upstream end 41 and a downstream end 42. Collar 40 includes clamp 44 located at the downstream end 42 of collar 40. In a preferred embodiment, the downstream end 40 of collar 40 includes lip 45. Lip 45 acts to retain clamp 44 on body 43 of collar 40. However, clamp 44 is free to rotate around body 43 of collar 40. Lip 45 is preferably a knurl or curve fabricated in the aluminum tubing at the downstream end 42 of collar 40. Lip 45 preferably has a diameter greater than the diameter of clamp 43 whereby lip 45 works to retain clamp 44 on collar body 43. In a preferred embodiment, a gasket 46 or sealing ring is disposed around collar body 43 between lip 45 and clamp 44. As shown, clamp 44 may include bolt holes 47 adapted to receive fasteners (not shown) from canister 50. Fasteners such as bolts may act to secure canister 50 to collar 40.

At various points in this description the system or components of the system are referred to with reference to an upstream or downstream position. Upstream refers generally to a direction or position toward the air source such as the gas turbine engine 10 or bleed valve 11. Downstream refers generally to a direction or position toward the vacuum source such as vacuum pump 70. In operation air flows through the system in a generally upstream to downstream direction.

Still referring to FIG. 2 the upstream end 41 of collar 40 includes hose fitting 48. In a preferred embodiment, hose fitting 48 is a polymer or plastic fitting adapted to receive source hose 20. Preferably hose fitting 48 may comprise a polypropylene banjo clamp. Hose fitting 48 is secured to body 43 of collar 40. Preferably hose fitting 48 is glued to body 43 of collar 40 to form a substantially airtight seal where hose fitting 48 attaches to body 43. Hose fitting 48 may itself include mating surface 49 adapted to receive source hose 20. When not in use, an end cap may be secured to end 41 and retained via mating surface 49.

When hose fitting 48 is selected as a polypropylene banjo clamp, a corresponding banjo clamp may be used with the end of source hose 20 that attaches to collar 40 to facilitate the attachment of source hose 20 to collar 40.

As also shown in FIG. 2 collar may include one or more sample ports 39. Sample ports 39 are useful for taking air samples or for measuring conditions in the air at the interior of collar 40. A thermocouple or pressure gauge may be disposed at sample port 39 for measuring air conditions within collar 40.

In a preferred embodiment a sample port 39 is positioned on body 43 of said collar 40. However, in a further embodiment a sample port may be positioned at other locations in the high volume air sampling system. For example a sample port 39 may be positioned on source hose 20 or tubing 60. A sample port 39 is useful for measuring air conditions such as temperature and pressure.

Referring now to the schematic of the high volume system shown in FIG. 1 collar 40 is affixed to canister 50. Canister 50 represents any of the commercially available or known sampling canisters used to collect or detect airborne contaminants. For example, canister 50 may contain reactive or adsorbent material. When contaminated air is passed through canister 50 airborne contaminants adhere to or otherwise react with the contents of canister 50. In this way canister 50 can later be analyzed to determine the nature of the airborne contaminant. Further, a measurement of the air volume passing through canister allows calculation of the concentration of the airborne contaminant.

Downstream from canister 50 is tubing 60 that is connected to a vacuum source such as vacuum pump 70. Tubing 60 provides the vacuum supply from vacuum pump 70 to canister 50. Air may exit from the air sampling system through vent 80.

In operation, source hose 20 is secured to collar 40. Source hose 20, having two ends, may be secured to collar 40 by affixing an end of source hose 20 at mating surface 49 of hose fitting 48. A preferred means of securing source hose 20 to hose fitting 48 includes use of a ring clamp (not shown). Mating surface 49 acts to provide a substantially airtight seal when source hose 20 is secured to collar 40. Source hose 20 is further disposed so that its other end is positioned to receive an air supply such as provided by bleed valve 11. In this way source hose 20 transmits an air sample from an upstream position to a downstream position.

In operation clamp 44 of collar 40 is affixed to canister 50. The action of affixing clamp 44 to canister 50 acts to press gasket 46 between lip 45 and clamp 44 thereby resulting in a substantially airtight seal between collar 40 and canister 50. As a result air contamination of an air sample from the joint between collar 40 and canister 50 is minimal.

In operation an air sample is taken by drawing air from a turbine engine's bleed valve 11 or bleed valves. The bleed valve 11 provides air when the engine 10 is running. Preferably the equipment for the high volume air sampler is attached before the engine 10 is operational. At a downstream position from the engine a vacuum source such as vacuum pump 70 pulls air through the system. As the air sample passes through the system, the air will pass through canister 50. Impurities in the air react with or otherwise are detected by canister 50. Canister 50 thus provides a measurement of targeted impurities in the air sample. Alternatively, canister 50 may be further analyzed to determine the presence and concentration of impurities in the air sample.

At various points in the description a seal or joint between system components is described as an airtight seal or a substantially airtight seal. Such a seal is not meant to be absolutely airtight so that no air whatsoever will pass through the seal when the system is in operation. Rather an airtight seal or substantially airtight seal means such a degree of seal that air contamination through the seal does not affect the analytical testing of the air sample in the system in any statistically significant way. Any leakage of air through a substantially airtight seal does not affect analysis of the air sample.

A first advantage of the high volume air sampler described herein is the ability to take a high volume air sample from a high volume air supply in a turbine jet engine using known and available sampling canisters. Additionally this advantage includes the ability to draw a high volume air sample in an otherwise closed environment such as the interior of an airplane.

A further advantage of the high volume air sampler system described herein is the ability to acquire an air sample with suspected impurities without drawing in air from other sources that are not suspected to be contaminated. In other words the sampling system focuses the collection of suspect air to the source of suspect air.

Still a further advantage of the air sampling system is the flexibility whereby suspect air may be gathered at a suspect engine or bleed valve.

Another advantage of the air sampling system is the inherent adaptability whereby flexible hose may be used to transport an air sample from a remote location, such as an engine compartment or high pressure start connection, to a more suitable human work station for collection and analysis.

It is also advantageous that the air sampling system is portable and easily used.

The materials used to construct the air sampling system are as described or above or of other materials suitable for use with air handling equipment.

Pressure Reduction Apparatus

Figure 3:
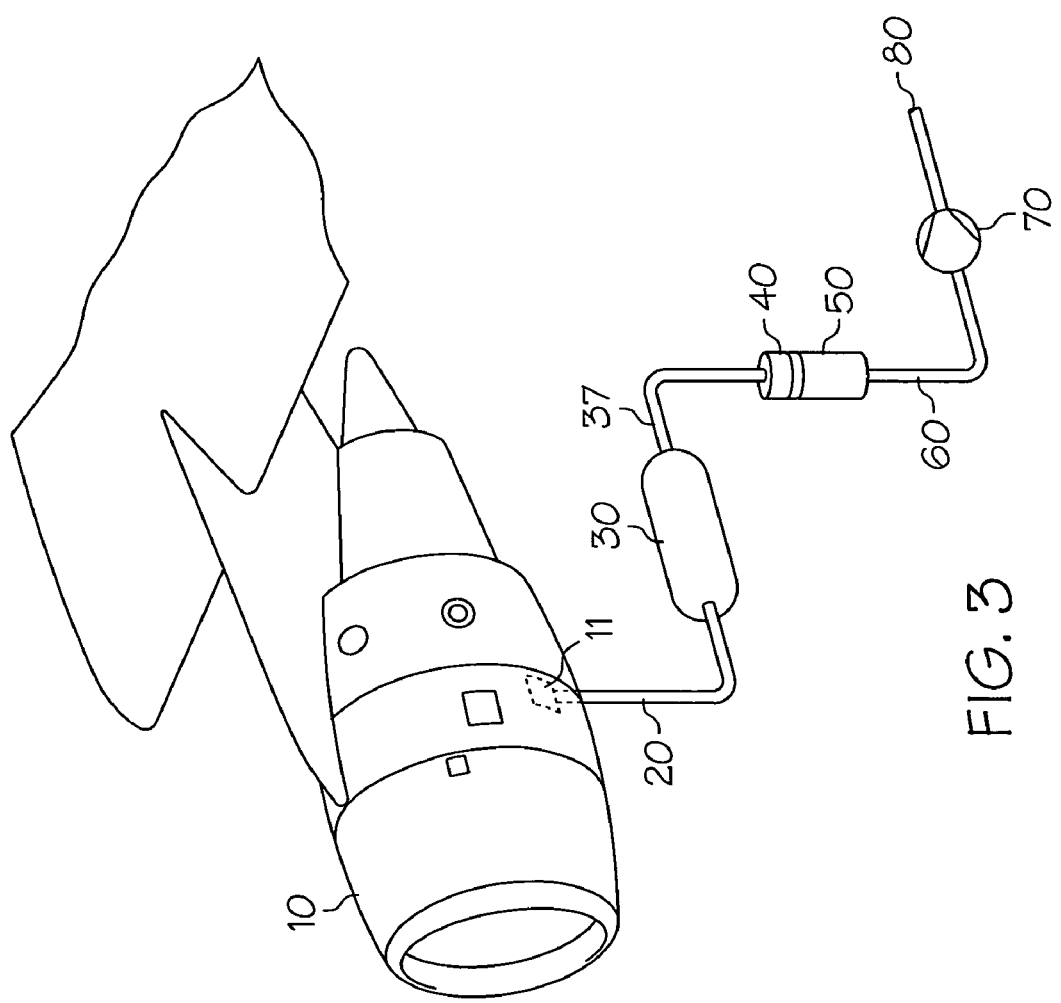
FIG. 3 is a schematic view of a high volume air sampler with a pressure reduction apparatus in accordance with an embodiment of the invention.

In an alternative embodiment shown in FIG. 3, source hose 20 transfers air from bleed valve 11 to a pressure reduction apparatus 30 before proceeding downstream to collar 40 and other sampling equipment.

Air from the bleed valve or compressor section of a gas turbine engine is typically at a higher temperature and pressure than atmospheric air. The temperature and pressure conditions of bleed air may present practical challenges to the air handling equipment widely used for taking and processing samples as well as safety hazards to the human operators using the equipment. In some embodiments it may be desirable to first reduce the temperature and pressure of the source air.

Source hose 20 provides a fluid conduit through which air from an air source such as a turbine engine bleed valve 11 passes to pressure reduction apparatus 30. Source hose 20 should be of a dimension and material adequate to provide the strength necessary to handle air at elevated temperatures and pressures. In aircraft engine applications the temperature and pressure are those associated with various compressor stages of the turbine engine, which can vary depending on the engine type. Material such as stainless steel may be used. However, if not using stainless steel, it is preferred that source hose 20 be constructed of a carbon impregnated teflon or carbon impregnated silicone after the sample temperature has reached a temperature and pressure within the rated limits of the source hose. These preferred materials assist in the avoidance of static charge buildup.

Figure 4:
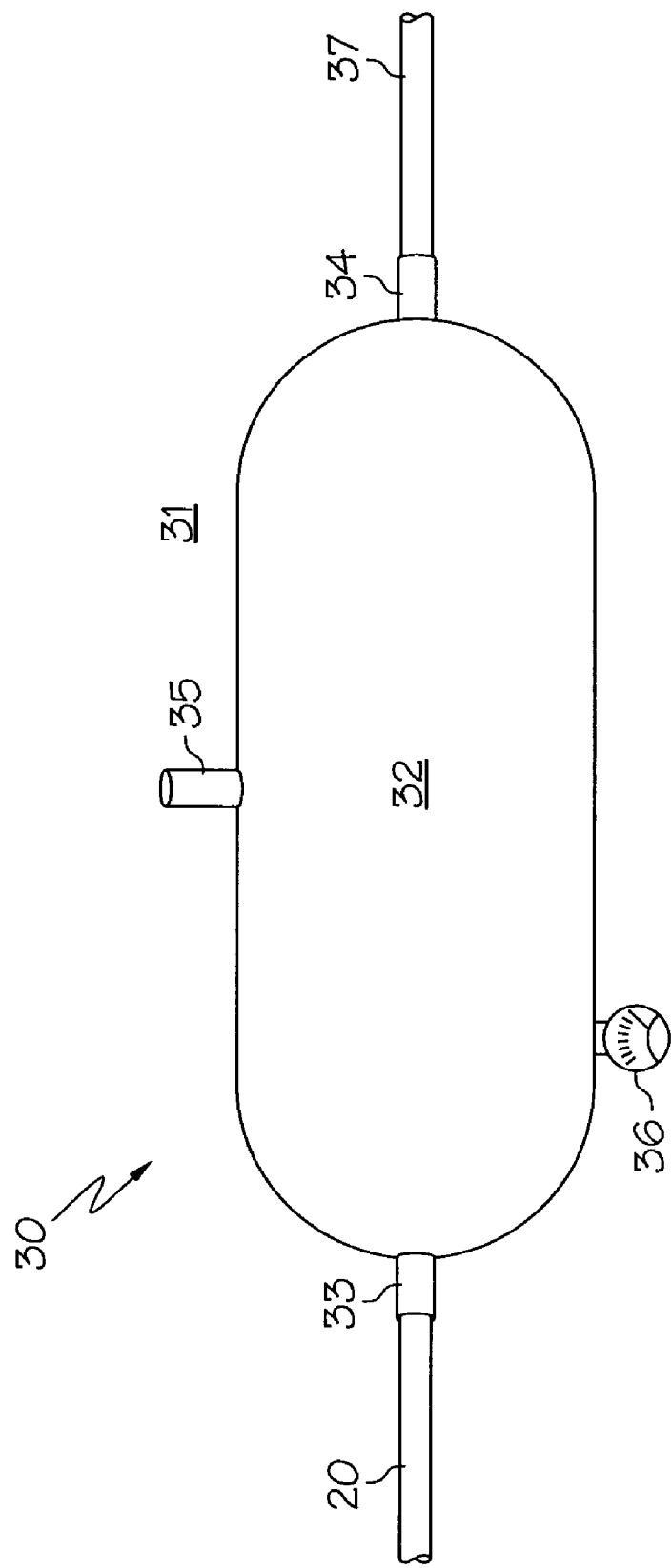
FIG. 4 is a detailed view of a pressure reduction apparatus in accordance with an embodiment of the invention.

As shown in FIG. 4 one component of the high volume air sampler system may include pressure reduction apparatus or pressure reducer 30. Pressure reducer 30 comprises a hollow vessel defining an exterior 31 and an interior 32 with apertures or ports providing fluid communication between the exterior and the interior of said vessel. Various geometries may be used in constructing pressure reducer 30 including spherical, cubic, and other three dimensional configurations. In one embodiment, pressure reduction apparatus 30 is cylindrical or drum-like in shape. In a preferred embodiment, pressure reduction apparatus 30 is comprised of aluminum. Aluminum and other aeronautical alloys are preferred in airplane applications for weight considerations. Other metallic or rigid materials may also be used.

As shown in FIG. 4 pressure reduction apparatus 30 includes in one embodiment inlet 33, outlet 34, and sample port 35. Air from the bleed valve 11 or other air source is directed to the interior of pressure reduction apparatus 30 through inlet 33. Optionally, pressure reduction apparatus 30 may include other ports or apertures providing fluid access to the interior of said apparatus.

Inlet 33, outlet 34, and sample port 35 may be of any dimension or diameter. A three inch diameter size is preferred, however, as this matches the dimension for common industrial air handling equipment. Also, preferably, sample port 35 inlet 33, and outlet 34 may include a lip or protrusion (not shown) as a structure on which to attach any flexible hose or line to such port.

Other equipment such as a valve, ball valve, one way valve or check valve may be included on any of the ports. In particular it is preferred that ball valves be used at inlet 33 and sample port 35 so as to prevent backflow of air from sample port 35 of pressure reduction apparatus 30 to sample port 35 when sampling from inlet 33 at low pressure. Additionally, a pressure gauge 3.6 may be affixed to pressure reduction apparatus 40. Pressure gauge 36 may provide, for example, a digital or analog read out of the interior pressure of pressure reduction apparatus. Likewise a thermocouple (not shown) or other temperature sensitive device may also provide a reading of the temperature at a chosen location such as the interior of the apparatus.

The dimensions of pressure reduction apparatus 30 are such that the temperature and pressure of the air drawn from the apparatus through outlet 34 are reduced from the temperature and pressure of air that is admitted into the apparatus through inlet 33. The degree of pressure and temperature reduction may vary depending on the size and design of the pressure reduction apparatus. The pressure and temperature reduction achieved by the pressure reducer 30 is adequate to allow safe and proper sampling and handling of the air sample by other equipment in the air sampling system. In a preferred embodiment the physical conditions of the air drawn from sample port are close to atmospheric pressures and temperatures up to 150 deg. F.

When an air sampling system includes pressure reduction apparatus 30 an additional hose or tubing will be required to transfer air from pressure reducer 30 to downstream equipment such as collar 40. FIG. 3 shows this as transfer tubing 37. Transfer tubing 37 provides a channel through which air is drawn from pressure reduction apparatus 30 and directed to any remainder of the air sampling system. Transfer tubing 37 can be the same as source hose 20. Preferably transfer tubing 37 is a flexible aluminum tubing of three inch diameter. This is stated as the preferred property for transfer tubing 37 as this represents a standard industrial size for air handling equipment. Other dimensions and materials may be chosen. Flexible aluminum tubing allows easy movement and positioning of transfer tubing 37.

In operation an air sample passes from an upstream position through pressure reducer 30 to a downstream position. As an air sample enters pressure reducer 30, the air encounters an environment that allows relatively high pressure and high temperature air to expand in the interior 32 of pressure reducer 30. In expanding, the air sample reduces in pressure and temperature. The air at reduced temperature and pressure then exits pressure reducer to a downstream position.

If desired, pressure reducer may include supplemental cooling equipment such as radiator fins and/or heat exchangers in order to remove heat accumulated within pressure reducer 30. In a preferred embodiment, pressure reducer 30 provides adequate cooling and heat exchange through radiant heat loss from the surface area of pressure reducer.

A first advantage of the temperature reduction apparatus described herein is the reduction in air temperature and pressure realized from air drawn from a high volume source such as a gas turbine engine or a bleed valve on a gas turbine engine.

A further advantage of the pressure reduction apparatus is the gain in safety realized from the temperature and pressure drop.

Still a further advantage of the pressure reduction apparatus is the ability to use conventional air testing equipment upon the reduction in temperature and pressure realized by the device.

The materials that are used to construct the pressure reduction apparatus are as described herein or those suitable for use in the airline industry.

Air Sampling from Air Conditioning Vent

Figure 5:
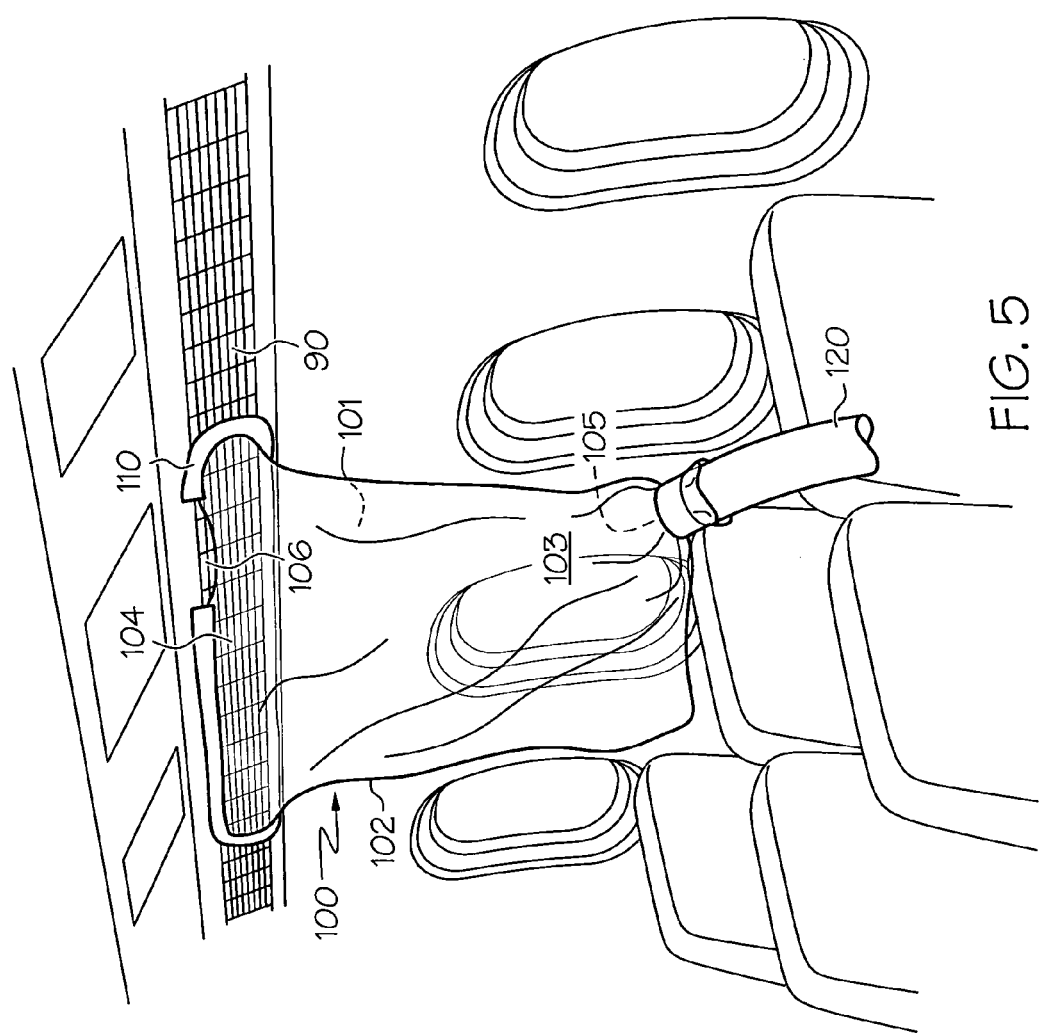
FIG. 5 is a schematic view of an air sampler with a collection bag in accordance with an embodiment of the invention.

Referring now to FIG. 5 there is shown a schematic diagram of an embodiment of the apparatus used for sampling low pressure air with high volume air collection equipment. An air source such as air conditioning vent 90 provides a source of air that is to be tested. In the passenger airplane environment one set of such air conditioning vents are typically located along the wall of the fuselage above the windows proximate to the passengers' heads. Collection bag 100 is positioned around a vent 90 or set of vents from which it is desired to collect an air sample.

Collection bag 100 preferably defines a body 103 and two openings, collection opening 104 and exit 105. Collection bag 100 thus defines an interior 101 and an exterior 102 relative to the collection bag. Collection bag 100 is formed of a material that prevents air that enters collection bag 100 from escaping collection bag 100 through body 103. Air is free to flow through collection opening 104 and exit 105. Further collection bag 100 is flexible and pliable so that its shape can be adapted to a variety of shapes and configurations.

Collection bag 100 is constructed of a durable and flexible material. Preferred materials are DuPont Tedlar® or Teflon®. Additionally material choice for collection bag 100 should minimize any residual hydrocarbons or volatiles in the construction material itself. Preferably collection bag 100 is made of an inert material that does not impart any volatile materials into the air sample passing through the collection bag interior 101. In other words collection bag 100 material of construction should not affect the level of impurities in the air sample itself. Thus additional preferred materials for construction of collection bag 100 are polymeric and plastic materials provided that they have the required inertness and low volatiles. Metal/plastic laminates may also be utilized.

Collection opening 104 of collection bag 100 is adaptable to cover air conditioning vent 90. Thus the size of collection bag 100 and of collection opening 104 is somewhat dependent on the vent size to be sampled. It has been found that collection bag 100 may be made of a standard size for ease of manufacturing and human handling. If a size larger than a standard size is required, multiple collection bags may be joined together as described further below.

Referring again to FIG. 5 fastener 110 affixes collection bag opening 104 around air conditioning vent 90. Preferably fastener 110 comprises a tape material suitable for use on aircraft. A tape should be selected that provides good adhesion to both collection bag 100 and the airplane vent structure. Collection bag 100 is affixed around air conditioning vent 90 such that air exiting vent 90 passes to the interior 101 of collection bag 100. As indicated, collection opening 104 is positioned around the particular vent or vent section from which it is desired to draw an air sample. Closure of collection opening 104 around vent 90 by fastener 110 prevents air from another source from entering collection bag interior 101.

In a preferred embodiment, fastener 110 comprises an aluminum tape. Tapes and adhesives for use as fastener 110 should be selected and applied in order to minimize any volatile materials or hydrocarbons that may otherwise enter the interior 101 of collection bag 100. The tacky portion of tape may include volatile materials. Nevertheless the method of operation employed with the collection of air samples may minimize the presence of such volatile materials in the air sample as described below.

As further shown in FIG. 5 tubing 120 is affixed to collection bag 100 at exit 105. Tubing 120 is affixed to collection bag 100 by fastener 110. Again fastener 110 preferably comprises an aluminum tape as previously described. Tubing 120 comprises a hollow conduit to move an air sample gathered in collection bag 100 to a further downstream position. In a preferred embodiment tubing 120 comprises flexible aluminum conduit. The flexibility of the conduit allows tubing 120 to snake through different airplane configurations to a desired destination.

Tubing 120 has two ends, a first end or upstream end, and a second, downstream end. Each end of tubing 120 has an opening. Tubing 120 allows fluid movement therethrough. Upstream end of tubing 120 is affixed to collection bag 100. Preferably the opening of tubing 100 at upstream end has sufficient rigidity so that collection bag exit 105 can be affixed around the upstream opening, and preferably this affixing or connecting is accomplished by fastener 110 such as tape. Thus upstream opening of tubing provides sufficient structure to withstand taping collection bag exit 105 to tubing. If necessary, fixtures or end pieces may be attached to tubing 120 to provide a sufficiently rigid structure on which to fasten collection bag 100.

With respect to the high volume air sample there is described a tubing 50, and with respect to the pressure reduction apparatus there is described a tubing 37; additionally there is described a tubing 120 with respect to use with collection bag 100. For clarification purposes it is noted that each such tubing may be the same, a flexible aluminum conduit. Alternatively, each such tubing may be different. Preferably, tubing 50, tubing 37, and tubing 120 operate at temperatures and pressures lower than that used with source hose 20, and accordingly tubing 50, tubing 37, and tubing 120 may be different from source hose 20.

Collection bag exit 105 preferably is fastened to tubing 120 so as to provide a fluid passage between the interior 101 of collection bag 100 and tubing 120. Preferably collection bag 100 is affixed to tubing 120 so as to provide a substantially airtight seal. The seal between collection bag 100 and tubing 120 prevents air from a source different from that provided by air conditioning vent 90 from entering into tubing through the tubing/collection bag joint. The preferred embodiment of the collection bag is Tedlar® or similar material.

Tubing 120 leads the air sample to a downstream point such as testing equipment as described herein, or other analysis equipment. Thus, tubing 120 may be connected to collar 40 for providing an air supply to a canister 50. A vacuum source such as a vacuum pump 70 is included at a point downstream of tubing 120. A vacuum supply to the downstream end of tubing 120 provides the necessary vacuum to draw an air sample provided by air conditioning vent 90 through collection bag 100 out of collection bag exit 105 and into tubing 120.

In operation fastener 110 should preferably secure collection bag 100 around vent 90 so as to prevent air from the collection bag exterior 102 from being drawn into the collection bag interior 101 other than what air is supplied to the interior from vent 90. The application of tape or aluminum tape as fastener 110 should be done in a way to minimize the volatile materials in the tape adhesive from appearing in the air sample. This is accomplished in part by minimizing the presence of any tape or adhesive in the interior 101 portion of collection bag 100. Volatiles are also limited in the way in which collection bag is inflated.

In use air is supplied at air conditioning vent 90 at a given rate of flow. In this manner air flows from vent 90 into the interior 101 of collection bag 100 and tends to inflate collection bag 100. The rate of inflow from vent 90 can be controlled by operation of the aircraft's air conditioning system. Additionally, air is withdrawn from the interior 101 of collection bag 100 through exit 105. Air is withdrawn by applying a vacuum to tubing 120, as by a vacuum pump 70 attached to tubing 120 whereby the vacuum operates on tubing 120 and collection bag 100. The rate of air withdrawal through exit 105 can be controlled by the level of vacuum applied to collection bag 100. Preferably the rate of inflow into collection bag interior 101 and the rate of outflow through collection bag exit 105 are controlled so that the interior 101 of collection bag remains in an inflated condition. Inflow is controlled to exceed outflow. In order to balance the greater flow of air coming from vent 90 with the lesser flow of air passing out of exit 105, the method may further use an overflow escape 106. Overflow escape 106 may comprise a space where collection opening 104 is not secured to the airplane surface thus providing a pathway for escape of excess air pressure from collection bag interior 101. Alternatively overflow escape 106 may comprise a port or hole provided in body 103 of collection bag 100 through which air may escape. Maintenance of collection bag 100 in an inflated condition in this way further assures that the air sample is being drawn from air supplied by vent 90 and not from any other air source. Further the inflation of collection bag 90 provides a useful visual indication that the air sampling method is working properly.

As mentioned, in a preferred embodiment, collection bags are manufactured in a given preferred size. This size may not accommodate all vent sizes, however. In such a situation multiple collection bags may be fastened together to reach the desired size. In this method, a first collection bag is cut along body 103 beginning at collection opening 104. A second collection bag is similarly cut along body 103 also beginning at collection opening. The cut along each body creates a first fold and a second fold in each collection bag. The first collection bag and second collection bag are then fastened together along common folds. The result is that collection opening on each bag has been enlarged. This enlarged opening may then be fastened around the air conditioning vent.

The start up of the air sampling method may include a period for adjustments made to the airflow balance to assure proper inflation of collection bag 100. Additionally, once collection bag 100 has been inflated, it may be desirable to run air through collection bag 100 for a period of time in order to purge any contaminants or volatiles that may have migrated to the interior 101 whether from a source such as fastener tape or non-targeted air. It may thus be desirable to delay the use of any air sampling equipment such as canisters and PUF cartridges until the proper air flow balance has been achieved within collection bag and a purge period has passed. Once such start up conditions have passed sampling equipment may then be attached to the sampling train at a position downstream of collection bag 100.

A first advantage of the apparatus and method for sampling air described herein is the ability to collect a low pressure air sample using high volume air sampling equipment. Additionally the apparatus may be adapted to collecting an air sample from an air conditioning vent located on a passenger aircraft.

A further advantage of the apparatus and method described herein is the fact that the equipment is lightweight and adaptable to various aircraft configurations.

Still a further advantage of the apparatus and method described herein is that an air sample may be taken from a particular air conditioning vent without contamination of that sample with air from another source.

Further, while the invention has been described with reference to a preferred embodiment or embodiments, those skilled in the art will understand that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. A high volume air sampler system for use on an aircraft comprising:
   an air source;
   a turbine engine bleed valve coupled to said air source;
   a source hose coupled to said bleed valve;
   a pressure reduction apparatus coupled to said source hose, the pressure reduction apparatus comprising:
      a hollow vessel coupled to said source hose, said hollow vessel including an interior and an exterior, an inlet, and a port to allow air to exit the vessel; and
      a valve affixed to said inlet to allow air to enter said vessel and to prevent air from exiting said vessel through said valve; and
   a high volume air sampler coupled to and disposed downstream of said pressure reduction apparatus, said high volume air sampler comprising:
      an adapter coupled to said pressure reduction apparatus, said adapter including a body having a first section, a second section, and an interior surface defining a cavity, said body first section having an opening formed therein that is in communication with said cavity, said body second section having a sample port formed therein that is in communication with said cavity, said sample port having a diameter that is smaller than the diameter of the opening; and
      a canister coupled to said adapter having an inlet opening, an exit opening, an interior region that defines a passage between said inlet and exit openings, and an adsorbent material disposed within said passage.

2. The system according to claim 1 wherein said valve prevents air from exiting said vessel through said valve.

3. The system according to claim 1 wherein said valve comprises a ball valve.

4. The system according to claim 1 wherein said apparatus comprises aluminum.

5. The system according to claim 1 wherein said apparatus comprises aluminum alloy.

6. The system according to claim 1 further comprising a pressure gauge for measuring air pressure in the interior of said vessel.

7. The system according to claim 1 further comprising a temperature gauge for measuring air temperature in the interior of said vessel.

8. A high volume air sampler system for reducing the temperature and pressure in air drawn from a gas turbine engine comprising:
   a pressure reduction apparatus comprising:
      a vessel body configured to receive the air from the gas turbine engine having an exterior, a substantially hollow interior, and an exit port providing fluid communication between the interior and the exterior of said vessel body; and a valve affixed to said vessel body providing fluid communication between the exterior and the interior of said vessel body wherein said valve permits air to enter said vessel body and prevents air from exiting said vessel body;

a transfer tubing coupled to said valve; and a high volume air sampler coupled to said transfer tubing said high volume air sampler comprising:

an adapter coupled to said transfer tubing, said adapter including a body having a first section, a second section, and an interior surface defining a cavity, said body first section having an opening formed therein that is in communication with said cavity, said body second section having a sample port formed therein that is in communication with said cavity, said sample port having a diameter that is smaller than the diameter of the opening; and a canister coupled to said adapter having an inlet opening, an exit opening, an interior region that defines a passage between said inlet and exit openings, and an adsorbent material disposed within said passage.

9. The system according to claim 8 wherein said vessel body is of sufficient dimension such that air entering said vessel body is reduced in pressure and temperature in the interior of said vessel body.

10. The system according to claim 8 wherein the interior of said vessel body defines a sufficient volume such that air admitted to said vessel body from a gas turbine engine is sufficiently reduced in temperature and pressure at the interior of said vessel body for testing for the presence of inorganic compounds.

11. The system according to claim 8 wherein the interior of said vessel body defines a sufficient volume such that air admitted to said vessel body from a gas turbine engine bleed valve is reduced in temperature and pressure at the interior of said vessel body to approximately ambient conditions.

12. The system according to claim 8 wherein said vessel body is composed partially of aluminum.

13. The system according to claim 8 where said vessel body is composed partially of aluminum alloy.

14. The system according to claim 8 where said vessel body is composed partially of stainless steel.

15. The system according to claim 8 further comprising a second valve affixed to the exit port of said vessel body wherein said second valve allows air to exit said vessel body and prevents air from entering said vessel body through said exit port.

16. A high volume air sampler system for reducing the temperature and pressure in air drawn from a bleed valve of a gas turbine engine comprising:

a pressure reduction apparatus comprising:

a vessel configured to receive air from the gas turbine engine, the vessel having an exterior and a substantially hollow interior; and a valve affixed to said vessel allowing air to enter said vessel and preventing air from exiting said vessel through said valve;

said vessel further defining a port to allow air to exit said vessel;

a hollow duct with two ends, a first end of said duct drawing air from a bleed valve of a gas turbine engine and a second end of said duct attached to said valve of said vessel;

a hollow tubing with two ends, a first end of said tubing affixed to the port of said vessel, and a second end; and a high volume air sampler coupled to said second end of said hollow tubing, said high volume air sampler comprising:

an adapter coupled to said hollow tubing, said adapter including a body having a first section, a second section, and an interior surface defining a cavity, said body first section having an opening formed therein that is in communication with said cavity, said body second section having a sample port formed therein that is in communication with said cavity, said sample port having a diameter that is smaller than the diameter of the opening; and a canister coupled to said adapter having an inlet opening, an exit opening, an interior region that defines a passage between said inlet and exit openings, and an adsorbent material disposed within said passage.

17. The system according to claim 16 wherein said hollow duct comprises a carbon impregnated Teflon.

18. The system according to claim 16 wherein said hollow duct comprises carbon impregnated silicone.

19. The system according to claim 16 further comprising a second valve affixed to the port of said vessel.

20. The system according to claim 16 wherein said vessel further defines an aperture providing fluid communication between the exterior and the interior of said vessel.

21. A method for sampling a high volume of air from a gas turbine engine, the method comprising the steps of:

directing air at a starting temperature and pressure from the gas turbine engine through a hollow duct;

providing a pressure reduction vessel with an exterior and having a hollow interior;

admitting air from said hollow duct into the interior of said pressure reduction vessel; and leading air from the interior of said vessel at a reduced temperature and pressure relative to the starting temperature and pressure, through a hose, to a high volume air sampler comprising an adapter and a canister, said adapter coupled to the pressure reduction vessel and including a body having a first section, a second section, and an interior surface defining a cavity, said body first section having an opening formed therein that is in communication with said cavity, said body second section having a sample port formed therein that is in communication with said cavity, said sample port having a diameter that is smaller than the diameter of the opening, and said canister coupled to said adapter having an inlet opening, an exit opening, an interior region that defines a passage between said inlet and exit openings, and an adsorbent material disposed within said.

22. The method according to claim 21 wherein the step of directing air at a starting temperature and pressure from a gas turbine engine through a hollow duct further comprises directing air from a bleed valve of a gas turbine engine at a starting temperature and pressure.

23. The method according to claim 21 wherein said pressure reduction vessel further comprises a valve and wherein the step of admitting air from said hollow duct into the interior of said pressure reduction vessel further comprises admitting air from said hollow duct through said valve into the interior of said pressure reduction vessel.

24. The method according to claim 21 further comprising the step of measuring the pressure of air at the interior of said pressure reduction vessel.

25. The method according to claim 21 further comprising the step of measuring the temperature of air at the interior of said pressure reduction vessel.

26. The method according to claim 21 wherein said pressure reduction vessel further comprises a sample port and further comprising the step of taking a sample of air from the interior of said pressure reduction vessel through said sample port.

* * * * *

UNITED STATES PATENT AND TRADEMARK OFFICE
CERTIFICATE OF CORRECTION

| | | |
|---|---|---|
| PATENT NO. | : 7,089,747 B2 | Page 1 of 1 |
| APPLICATION NO. | : 10/788763 | |
| DATED | : August 15, 2006 | |
| INVENTOR(S) | : Richard B. Fox | |

It is certified that error appears in the above-identified patent and that said Letters Patent is hereby corrected as shown below:

On The Title Page: Item (57)

In the last line of the ABSTRACT, delete the word "ad" and insert the word --and--.

In claim 21, column 14, line 53, insert the word --passage-- after the word "said" and before the period ".".

Signed and Sealed this

Twentieth Day of March, 2007

JON W. DUDAS
*Director of the United States Patent and Trademark Office*